United States Patent [19]

Barbier et al.

[11] Patent Number: 5,534,689
[45] Date of Patent: Jul. 9, 1996

[54] DEVICE TO CHECK THE SETTING OF THE POSITION AND ORIENTATION OF A HELMET WITH RESPECT TO THE HELMET WEARER'S HEAD

[75] Inventors: Bruno Barbier; Patrick Lach, both of Bordeaux; Alain Leger, Courbevoie, all of France

[73] Assignee: Sextant Avionique, Meudon La Foret, France

[21] Appl. No.: 377,828

[22] Filed: Jan. 25, 1995

[30] Foreign Application Priority Data

Jan. 25, 1994 [FR] France .................................. 94 00768

[51] Int. Cl.⁶ .................................................. G01C 21/02
[52] U.S. Cl. ..................... 250/206.2; 356/154; 351/210
[58] Field of Search ............................. 250/206.1, 206.2; 356/153, 154; 351/210

[56] References Cited

U.S. PATENT DOCUMENTS

| | | |
|---|---|---|
| 4,852,988 | 8/1989 | Velez et al. ............................. 351/210 |
| 5,053,764 | 10/1991 | Barbier et al. . |
| 5,057,744 | 10/1991 | Barbier et al. . |
| 5,093,567 | 3/1992 | Staveley ................................. 250/221 |
| 5,239,293 | 8/1993 | Barbier . |
| 5,313,054 | 5/1994 | Lach et al. . |
| 5,386,258 | 1/1995 | Nagano ................................... 354/400 |
| 5,410,376 | 4/1995 | Cornsweet et al. ..................... 351/210 |
| 5,428,413 | 6/1995 | Shindo .................................... 351/210 |

FOREIGN PATENT DOCUMENTS 2237215  2/1975  France .
2522804  9/1983  France .

Primary Examiner—Edward P. Westin
Assistant Examiner—Stephen Calogero
Attorney, Agent, or Firm—Oblon, Spivak, McClelland, Maier & Neustadt

[57] ABSTRACT

An instrument system to make settings and verify that the pupil of an eye of a wearer of a helmet designed to receive a piece of optoelectronic equipment itself having a pupil truly coincides with the wearer's pupil, wherein the instrument system includes first and second optical devices whose position with respect to the helmet is fixed, and a first screen and a second screen $E_1$ and $E_2$, each including a reference-marking test pattern, the position of the helmet with respect to the wearer being accurate only if the image of the wearer's eye through the first optical means and the image through the second optical means, of a target on which the wearer's line of view is fixed, are respectively well-positioned with respect to the test patterns of the screens $E_1$ and $E_2$. In the preferred embodiment, the screens $E_1$ and $E_2$ are merged into a single screen E through an optical device partially common to the first and second optical devices.

6 Claims, 2 Drawing Sheets

1

DEVICE TO CHECK THE SETTING OF THE POSITION AND ORIENTATION OF A HELMET WITH RESPECT TO THE HELMET WEARER'S HEAD

BACKGROUND OF THE INVENTION

1. Field of the Invention

The invention lies in the field of instrument systems designed to match an optronic system mounted on a helmet with the particular morphology of the helmet wearer. This matching constitutes the procedure for the customizing of the helmet. Such helmets are used particularly in military aeronautics.

Head equipment in military aeronautics consists essentially of the helmet whose primary function is to protect the pilot. The helmet is also used as a support for breathing and hearing instruments, and for a display system that provides the pilot with information by means of an image source (cathode-ray tube, liquid crystal matrix etc.) and an optical collimation system.

The helmet has to be designed for and matched with the pilot's morphology to provide for the optimal use of the head equipment. The matching of each helmet with its wearer's morphology is done during the customizing procedure. During this procedure, the helmet has to be positioned and oriented very precisely in relation to anatomical reference points of the subject.

2. Description of the Prior Art

In the current state of the art, the customizing procedure calls for several operations for the precise identification of the pilot's morphology. The manufacture of the helmet can be done on the basis of this morphological information, but these operations are lengthy and imprecise because of the difficulty of making precise measurements of the characteristics of the head.

Other procedures call for active participation by the subject so that he or she positions his or her head with respect to precise reference points on the helmet or on an associated instrument system. During these procedures, there is a risk that the pilot might take up uncomfortable postures that do not correspond to functional positions that he or she will take up when using the equipment. These constraints in particular harm the subsequent efficiency of the display system which will be mounted on the helmet.

The aim of the customizing procedure is to place two optical diaphragms, a first diaphragm and a second diaphragm, in one and the same plane P. The first diaphragm is constituted by the pupil of the helmet wearer's eye. The second diaphragm is the pupil of the optical system that will be mounted on the helmet. This pupil of the optical system is in a plane P that has no physical existence but whose theoretical position is known in relation to reference points taken on the helmet, for example fastening points of the optronic display system.

It is imperative that the optical pupil of this system should be placed in the same plane as the pupil of the wearer's eye and that the two diaphragms constituted by the two pupils should be centered on each other when the subject looks in a reference direction $\vec{u}$. This direction is generally represented by a collimated target and is located in a horizontal plane passing through the line of the wearer's eyes during the customizing procedure.

The aim of the invention is to simplify and shorten the customizing procedure. The aim is also to preserve, for the wearer, a degree of ease and comfort during this procedure that is at least equal to the ease and comfort that he or she will enjoy when he or she is fully fitted out. Finally the aim is to improve the positioning precision of the helmet.

SUMMARY OF THE INVENTION

The object of the invention relates to an instrument system comprising optical means and an image sensor that keeps a fixed position with respect to a customizing helmet or with respect to the real helmet. A simple way of achieving this condition is to use a rigid mechanical structure to hold the instrument system, this rigid mechanical structure being fixed to the helmet, for example by using the fastening points designed for the optronic system. It is this simple method that is used in the preferred embodiment. The instrument system may furthermore be supported by an external arm so as to increase the wearer's comfort. It is possible for the instrument system to have no direct mechanical link with the helmet. The essential point is that the instrument system should constantly follow the movements of the helmet in having a known fixed position with respect to this helmet. It is this instrument system that will be used for the easy identification and checking of the position of the real helmet or of a customizing helmet with respect to the position of the wearer's pupil. It is also used for the easy identification of the orientation of the wearer's visual axis.

When the position and orientation of the real helmet or of the instrument system helmet have been set in such a way that the pupil of the wearer's eye coincides with the theoretical plane P containing the pupil of the optronic device to be mounted on the helmet, the making of the helmet can be completed, for example by the injection of a hardening foam that will adapt to the morphology of the wearer's head. The molding in position thus made will remain attached to the helmet if it is the real helmet or will be used to shape one or more other helmets if a special customizing helmet is used. In the latter case, it will also be possible to use the first molding made on the wearer's head to make other moldings suited to the wearer's morphology, these moldings requiring, for their manufacture, conditions that the wearer would not be able to withstand (such as temperature and pressure conditions and the presence of harmful products).

In short, the invention relates to an instrument system for setting and verifying a position of a helmet with respect to a position of a helmet wearer having, in a position of rest, a viewing direction defined by an axial direction $\vec{u}$, said helmet being designed to receive optronic instruments at a location physically represented by reference points on said helmet, said optronic instruments themselves having an optical pupil whose position with respect to the reference points is known, these optronic means also having an optical axis $\vec{v}$ whose direction with respect to said reference points is known, wherein the operations of setting and verification performed by said instrument system are aimed at verifying that the position of the wearer's pupil coincides with the position of the pupil of said optronic means and that the axial direction $\vec{u}$ of the wearer's line of view forms a predetermined angle with the optical axis $\vec{v}$ of said optronic means, said instrument system comprising:

first optical means designed to form an image of the pupil of the eye on a first screen $E_1$ on which there is made a first test pattern, a mechanical assembly formed by said first optical means and said first screen occupying a known fixed position with respect to said helmet, this position being such that a sharp image of the pupil of the wearer's eye centered on said first test pattern can be obtained only if the position of the pupil of the eye coincides with the position of the pupil of the optronic means to be mounted on the helmet, second optical means designed to bring about the one-to-one correspondence, between each spatial direction and a respective point on a second screen $E_2$ on which there is designed a second test pattern representing a figure, said second optical means and said second screen occupying a known fixed position with respect to the helmet, this position being such that a collimated figure located with respect to the wearer of the helmet in the direction $\vec{u}$ cannot have an image superimposed on said second test pattern unless said second optical means are oriented in a direction in which the axial direction $\vec{u}$ of the wearer's line of view and the axial direction $\vec{v}$ of the optical axis of said optronic means are oriented with respect to each other in said predetermined direction.

Advantageously, in the preferred embodiment, the screens $E_1$ and $E_2$ are merged into one and the same screen. The first and second optical means therefore have common optical means.

In the preferred embodiment, the helmet used is a special customizing helmet mounted on a mechanical assembly enabling, firstly, a translation of the helmet in three directions forming an orthonormal trihedron and, secondly, a rotation of the helmet about itself on three axes forming an orthonomal trihedron.

Mechanical assemblies such as this are well known in the prior art. This aspect shall not be touched upon in the following description of a preferred embodiment of the invention.

BRIEF DESCRIPTION OF THE DRAWINGS

This description shall be made with reference to the appended drawings. This description shall bring out other details and advantages of the invention. Of the drawings.

MORE DETAILED DESCRIPTION

Figure 1:
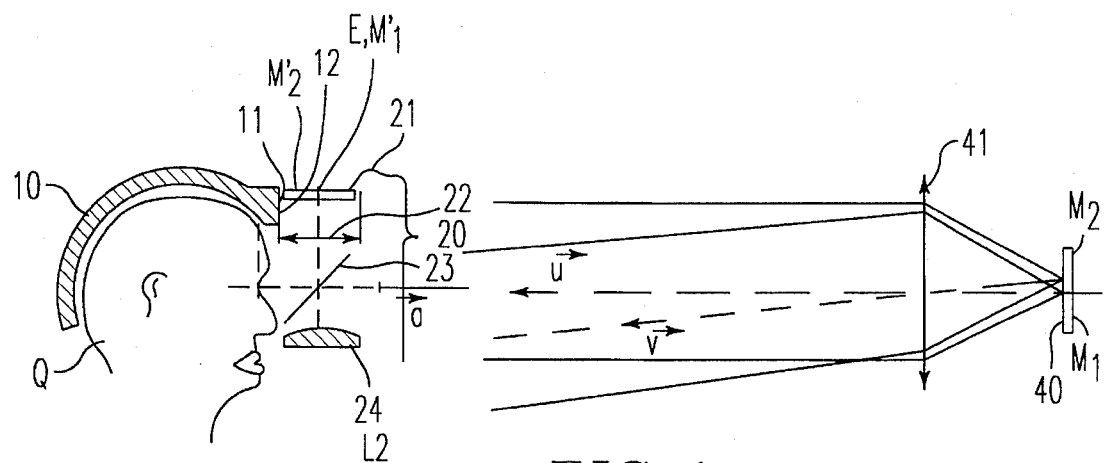
FIG. 1 is a drawing designed to illustrate the preferred embodiment of the invention.

FIG. 1 is a drawing designed to illustrate the preferred embodiment of the invention.

In this embodiment, an instrument system 20 according to the invention is fixed to a helmet structure 10 that reproduces the shape of a real helmet and is designed, after the verification of its position and its accurate orientation with respect to the head of the wearer who is referenced Q, to give a shape for the external part of a molding whose internal shape will be constituted by the external shape of the head of the wearer Q. Then, after reproduction, possibly in a different material, the shape of this molding will be transferred to the structure of one or more helmets which, by this transfer, will be matched with the wearer's morphology. As explained further above, this structure 10 is fixed in a known way to a mechanical assembly (not shown). This mechanical structure enables a translation of the structure 10 along three axes with sufficient clearance to enable heightwise, lateral, frontward and backward positional adjustments. FIG. 1 shows mechanical means related to the structure and having, with reference to this structure, the same position as the means for fastening the optronic means that have to be mounted on the helmet. FIG. 1 shows these mechanical means firstly by a reference face 11 and, secondly, by a set of anchoring pins 12, only one of which is shown. This reference face 11 and these anchoring pins 12 are used to fasten the first and second optical means as well as the single screen E by means of a rigid carrier structure that is not shown.

The fastening means 11–12 determine the position, with reference to a structure 10, of a plane P containing the optical pupil of the optronic means and their axial optical direction shown in FIG. 1 by a vector $\vec{v}$. This position is known at the outset by the design computations, and it can be checked by measurement means that are known per se.

As already explained here above, it is recalled that the instrument system 20 enables the real-time checking firstly of the centering of the pupil of the eye on the theoretical position of the instrument pupil of the display system and, secondly, the orientation of the central direction of this system with respect to a reference direction. During this procedure, the display system is not mounted on the helmet or the structure 10 but, after the procedure, it is certain that it will get positioned accurately with respect to the subject's anatomical reference points when it is fastened to the helmet.

So as to avoid any unnecessary confusion as regards the understanding of the description, the drawings do not show mechanical parts used for the connection, firstly of the elements that play a part in the making of the instrument system fixedly with one another and, secondly of the set of these elements to the mechanical elements 11, 12 of the structure 10. When it is stated that the relative position of the different elements constituting the instrument system with respect to one another and with respect to the structure 10 is fixed, this does not rule out the fact that this position is nevertheless adjustable. The adjusting or setting enables the same type of instrument system to be used for different types of helmets. For one and the same type of helmet, the same position of adjusting can be used.

The instrument system 20 includes the first and second optical means as well as the two screens $E_1$ and $E_2$. In the embodiment described herein, these two screens are merged into a single screen E referenced 21. In the preferred embodiment, the screen is constituted by a CCD (charge-coupled device). This screen makes it possible to retrieve and observe the image formed on the screen, on a control monitor easily accessible to a customizing operator. Naturally, this screen could be made on any known means, for example on a scattering surface whose images can be observed either directly or by means of an eyepiece.

Particular points may be physically represented beforehand on the surface of this screen. In the case of the preferred embodiment, these particular points are physically represented by an electronic test pattern that is superimposed on the image given by the electro-optical sensors. It is this electronic test pattern that enables the verification, by comparison, of the accurate location of images formed on the screen and, therefore, the verification of the accurate location of the structure 10 with reference to the head of the wearer Q. The first optical means are designed to form an image of the pupil of the eye of the wearer Q on the screen E21. In the case of the embodiment, they comprise a plane mirror 23 constituted, in this case, by a partially reflective plate and by a focusing means constituted, in the case of the embodiment, by a lens $L_1$ 22. When the eye of the wearer Q is accurately positioned in the plane P of the pupil of the optronic means, the center of the pupil of the eye should be at a point C identified beforehand on the screen.

Figure 2:
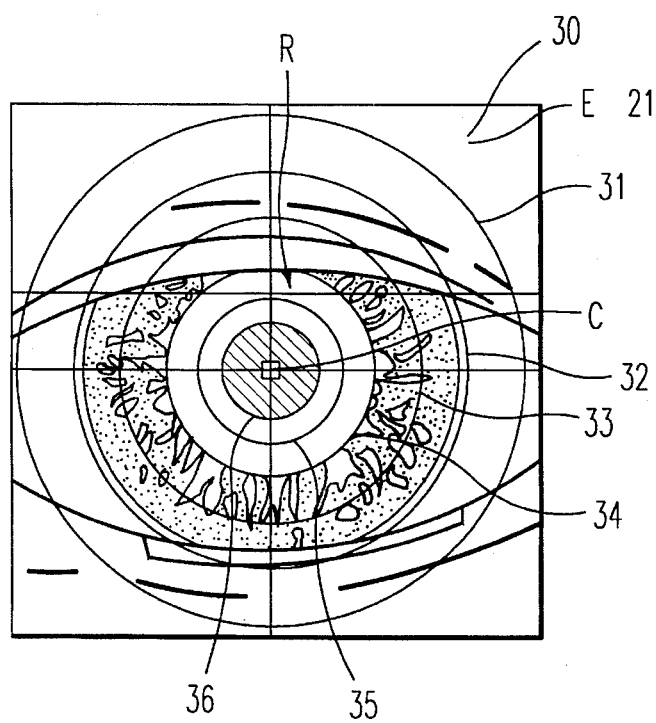
FIG. 2 shows the test pattern of a screen as well as a fictitious eye that is well-positioned with respect to the test pattern.

In the case of the embodiment, in addition to the point C, the position test pattern comprises concentric circles centered on C. An example of the image to be obtained is shown in FIG. 2. In this figure, the different concentric circles are referenced 31 to 36. An image of a well-centered fictitious eye is superimposed on the test pattern 30 constituted by the circles 31 to 36 and by the point C. This first setting is obtained by the triaxial translation of the structure 10.

The second optical means are also shown in FIG. 1. They comprise the lens $L_1$ 22 as well as a mirror which, in this case, is constituted by the partially reflective plate 23. The means 22 and 23 are therefore common to the first and second optical images. The second means furthermore comprise a spherical mirror 24. These are the second optical means that will make it possible to ensure that the relative orientation of the axis of the wearer's line of view and of the axis of the optronic means is accurate.

To this end, auxiliary means, constituted by a collimated target, are used. In the embodiment, this target is constituted by a screen 40 comprising two physically represented points $M_1$ and $M_2$. The screen is vertically mobile. A collimation unit 41 that is movable with the screen enables the one-to-one conversion, for an observer, of each point of the screen in one direction in space.

During the customizing procedure, the wearer Q is asked to look at the point $M_1$. As a result, the direction $\vec{u}$ of his line of view is physically represented on the screen 40 by the point $M_1$. The point $M_2$ corresponds to the direction $\vec{v}$.

The second optical means are arranged to bring about the one-to-one correspondence, with the directions $\vec{u}$ and $\vec{v}$, of the points $M'_1$ and $M'_2$ on the single screen E21. These points are prepositioned and form part of the test pattern 30.

In the preferred embodiment, the direction $\vec{u}$ is converted by the second optical means in a direction that corresponds to the optical axis of the second optical means. The direction $\vec{v}$ is converted by the second optical means in a direction $\vec{E}$. This direction $\vec{E}$ has a one-to-one correspondence, on the screen $\vec{E}$, to the point $M'_2$. The direction $\vec{E}$ in one of the test patterns 30 used to customize one type of helmet has a direction that corresponds to a direction $\vec{v}$ forming, with the direction $\vec{u}$, an angle of 3° in a vertical plane comprising the direction $\vec{u}$.

Figure 3:
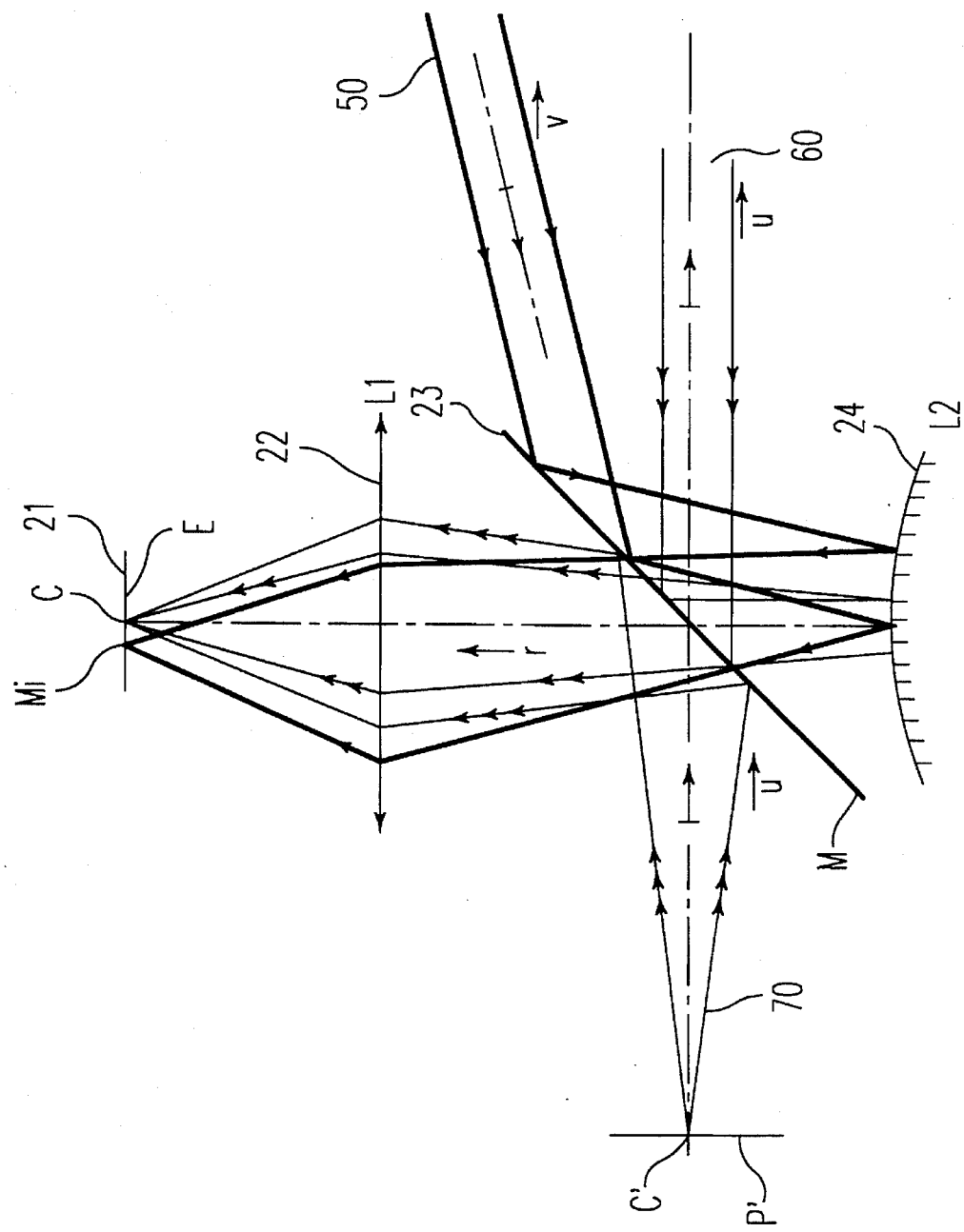
FIG. 3 shows the optical paths, starting from the wearer of the helmet and from an auxiliary target through the first and second optical means.

The optical functioning of the instrument system according to the invention shall now be explained with reference to FIG. 3.

This figure shows the combination of the three optical paths that get combined in the instrument system made.

The first path 50, whose rays are referenced by an arrow sign, is constituted by the rays coming from the direction $\vec{v}$ corresponding to the point $M_2$ on the screen 40. They get reflected on the mirror constituted by the semi-reflective plate 23 towards the spherical mirror $L_2$24. After reflection on $L_2$, the rays go through the plate 23 and are focused by the lens $L_1$22 towards the point $M'_2$ of the screen E21.

The second path 60, whose rays are referenced by two arrow signs, one located behind the other, is constituted by the rays coming from the direction $\vec{u}$ corresponding to the point M1 on the screen 40. After reflection on the mirror 23, they get reflected on the spherical mirror $L_2$24, go through the plate 23 and get focused by the lens 22 on the screen E at the point C.

The third optical path 70 comes from the wearer's eye. Its rays are represented by three arrows that follow one another. After reflection on the mirror 23, the rays are focused at the point C and are focused by the lens 22 on the screen E at the point C.

All the focusing points indicated here above for the screen E21 are the focusing points obtained when the helmet and, therefore, the optical instruments linked to it are accurately positioned in translation and in rotation.

The setting procedure takes place as follows:

the wearer is placed in a functional position, for example on a seat whose geometry represents the desired application, the subject's sole task is to fix his eye, throughout the procedure, on the particular point $M_1$ of the target that is localized before it, in the direction $\vec{u}$ known in the referential system of the laboratory, it will be ascertained that, under these conditions, the anatomical reference plane (the Frankfort plane) is located substantially in a horizontal position. If there is an excessive divergence, then a correction of the posture of the head must be made, the wearer holds his head still with respect to the referential system of the laboratory, in this functional position, an operator sets the position and orientation of the helmet 10 fitted out with the instrument system. The helmet 10 is also provided with a preform filling that is kept flexible at an appropriate temperature. The unit may by mounted on a three-translation/three-translation 3D machine capable of being handled by an operator.

The setting consists essentially in:

translating and orienting the helmet to obtain a sharp and centered image of the pupil of the subject's eye on the screen E (FIG. 2). The objective $L_1$ is chosen so that its field depth is in the range of the desired precision of the positioning of the optical pupil of the display system with respect to the pupil of the eye. The centering is done with respect to the reference points that get superimposed on the screen E, namely the concentric circles 31 to 36 and the point C, translating and orienting the helmet in such a way that the point that is the image of $M_2$ displayed on the screen E21 is superimposed on the point $M'_2$ of the test pattern.

A motion of translation or rotation may act simultaneously on the sharpness of the image of the pupil on the screen E21, its centering and the relative position of the image of the points $M_2$ and $M_1$ on the screen E. The operator must act alternately on the rotational and translational motions to converge simultaneously on the right position and right orientation of the helmet.

Once the three setting criteria are met, the helmet is kept still and the filling material is injected.

During this operation, the instrument system makes it possible to check the progress of the quality of the customization, through the real-time observation of the possible drifts in the centering of the pupil of the eye on C, its sharpness, and the superimposition of the points $M'_2$ and $C$, when the subject fixes his line of view on the point $M_1$.

An additional check lies in ascertaining that, on the screen $E21$, the point that is the image of the point $M_1$ of the target is truly superimposed with the reference $C$.

What is claimed is:

1. An instrument system for setting and verifying a position of a helmet with respect to a position of a helmet wearer having, in a position of rest, a viewing direction defined by an axial direction $\vec{u}$, said helmet being designed to received optronic instruments at a location physically represented by reference points on said helmet, said optronic instruments themselves having an optical pupil whose position with respect to the reference points is known, these optronic means also having an optical axis $\vec{v}$ whose direction with respect to said reference points is known, wherein the operations of setting and verification performed by said instrument system are aimed at verifying that the position of the wearer's pupil coincides with the position of the pupil of said optronic means and that the axial direction $\vec{u}$ of the wearer's line of view forms a predetermined angle with the optical axis $\vec{v}$ of said optronic means, said instrument system comprising:

first optical means designed to form an image of the pupil of the eye on a screen on which there is made a first test pattern, a mechanical assembly formed by said first optical means and said screen occupying a known fixed position with respect to said helmet, this position being such that sharp image of the pupil of the wearer's eye centered on said first test pattern can be obtained only if the position of the pupil of the eye coincides with the position of the pupil of the optronic means to be mounted on the helmet, second optical means designed to provide points on said screen which each correspond to each of said axial direction and said optical axis wherein said screen further contains a second test pattern representing a figure, with said second optical means occupying a known fixed position with respect to the helmet, this position being such that a collimated figure located with respect to the wearer of the helmet in the direction $\vec{u}$ cannot have an image superimposed on said second test pattern unless said second optical means are oriented in a direction in which the axial direction $\vec{u}$ of the wearer's line of view and the axial direction $\vec{v}$ of the optical axis of said optronic means are oriented with respect to each other in said predetermined direction.

2. An instrument system according to claim 1, wherein the first optical means comprise a mirror and a focusing means.

3. An instrument system according to claim 1, wherein the second optical means comprise a mirror and a focusing means.

4. An instrument system according to claim 1, wherein the first and second optical means comprising common optical means.

5. An instrument system according to claim 4, wherein the common means comprise a partially transparent plate and a focusing means, and wherein one of the first and second optical means furthermore comprises complementary focusing means.

6. An instrument system according to claim 5, wherein the complementary focusing means are constituted by a spherical mirror.

* * * * *